US010244762B1

(12) United States Patent
Lei et al.

(10) Patent No.: US 10,244,762 B1
(45) Date of Patent: Apr. 2, 2019

(54) SOLID AQUATIC ORGANISM CONTROL COMPOSITION AND METHOD OF USE

(71) Applicant: Arch Chemicals, Inc., Allendale, NJ (US)

(72) Inventors: Deqing Lei, Alpharetta, GA (US); Ryan Wersal, Cumming, GA (US)

(73) Assignee: Arch Chemicals, Inc., Allendale, NJ (US)

( * ) Notice: Subject to any disclaimer, the term of this patent is extended or adjusted under 35 U.S.C. 154(b) by 22 days.

(21) Appl. No.: 15/441,376

(22) Filed: Feb. 24, 2017

Related U.S. Application Data

(60) Provisional application No. 62/299,656, filed on Feb. 25, 2016.

(51) Int. Cl.
| | | |
|---|---|---|
| *A01N 59/00* | (2006.01) | |
| *A01N 37/02* | (2006.01) | |
| *A01N 59/16* | (2006.01) | |

(52) U.S. Cl.
CPC ............. *A01N 59/00* (2013.01); *A01N 37/02* (2013.01); *A01N 59/16* (2013.01)

(58) Field of Classification Search
None
See application file for complete search history.

(56) References Cited

U.S. PATENT DOCUMENTS

| | | | |
|---|---|---|---|
| 3,951,840 A | 4/1976 | Fujino et al. | |
| 3,963,634 A | 6/1976 | Tachibana et al. | |
| 4,119,557 A | 10/1978 | Postlethwaite | |
| 4,253,971 A * | 3/1981 | MacLeod | C02F 1/50 210/759 |
| 5,449,658 A * | 9/1995 | Unhoch | A01N 47/44 424/613 |
| 5,747,416 A | 5/1998 | McArdle | |
| 5,817,696 A * | 10/1998 | Zollinger | A01N 37/16 504/157 |
| 5,882,526 A * | 3/1999 | Brown | C02F 1/722 210/753 |
| 6,262,008 B1 | 7/2001 | Renvall et al. | |
| 6,267,979 B1 * | 7/2001 | Raad | A01N 37/44 424/405 |
| 6,582,605 B2 | 6/2003 | Krulik et al. | |
| 7,476,529 B2 | 1/2009 | Podella et al. | |
| 7,494,957 B2 | 2/2009 | Pena et al. | |
| 7,923,417 B2 | 4/2011 | Sanders et al. | |
| 8,178,742 B2 | 5/2012 | Innocenti et al. | |
| 8,323,949 B2 | 12/2012 | Podella | |
| 8,415,278 B2 | 4/2013 | Sanders et al. | |
| 8,871,682 B2 | 10/2014 | Podella et al. | |
| 2001/0048911 A1 | 12/2001 | Korvela et al. | |
| 2003/0136942 A1 | 7/2003 | Smith et al. | |
| 2006/0258535 A1 | 11/2006 | Larose | |
| 2007/0095760 A1 * | 5/2007 | Girvan | C02F 1/50 210/696 |
| 2008/0237149 A1 * | 10/2008 | Harvey | C02F 1/722 210/759 |
| 2008/0272063 A1 | 11/2008 | Boulos et al. | |
| 2010/0069245 A1 | 3/2010 | Scholer et al. | |
| 2010/0099599 A1 | 4/2010 | Michalow et al. | |
| 2011/0319341 A1 | 12/2011 | Awada | |
| 2012/0142530 A1 | 6/2012 | Michalow et al. | |
| 2014/0248373 A1 | 9/2014 | Michalow et al. | |
| 2015/0105257 A1 | 4/2015 | Ratajczyk et al. | |

FOREIGN PATENT DOCUMENTS

| | | | | |
|---|---|---|---|---|
| EP | 0517378 | | 12/1992 | |
| EP | 0702897 | | 3/1996 | |
| EP | 0786205 | A1 * | 7/1997 | ............. A01N 37/10 |
| WO | WO 01/60160 | | 8/2001 | |
| WO | WO 02/004360 | | 1/2002 | |
| WO | WO-2013044299 | A1 * | 4/2013 | ................ C02F 1/68 |

OTHER PUBLICATIONS

Sigma-Aldrich, "Ethylenediaminetetraacetic acid tetrasodium salt hydrate," Safety Data Sheet, Version 5.3, Revision Date: May 11, 2017, p. 1-7.*
Wisconsin Department of Natural Resources, "Chemical Fact Sheet: Simazine," published May 1990, pp. 1-4.
Wisconsin Department of Natural Resources, "Fluridone Chemical Fact Sheet," published Jan. 2012, p. 1-2.
BD Bionutrients™ Technical Manual, "Advanced Bioprocessing," Third Edition Revised, published Oct. 2006, pp. 1-68.

* cited by examiner

*Primary Examiner* — Monica A Shin
(74) *Attorney, Agent, or Firm* — Dority & Manning, P.A.

(57) ABSTRACT

A biocide contains a hydrogen peroxide producing compound, in combination with controlled amounts of a chelating agent and a peroxide enhancing agent. In one embodiment, the composition can be used to control an algae population in a water body. The chelating agent and the peroxide enhancing agent synergistically combine with the hydrogen peroxide producing compound to increase the potency and effectiveness of the oxidizer.

20 Claims, 1 Drawing Sheet

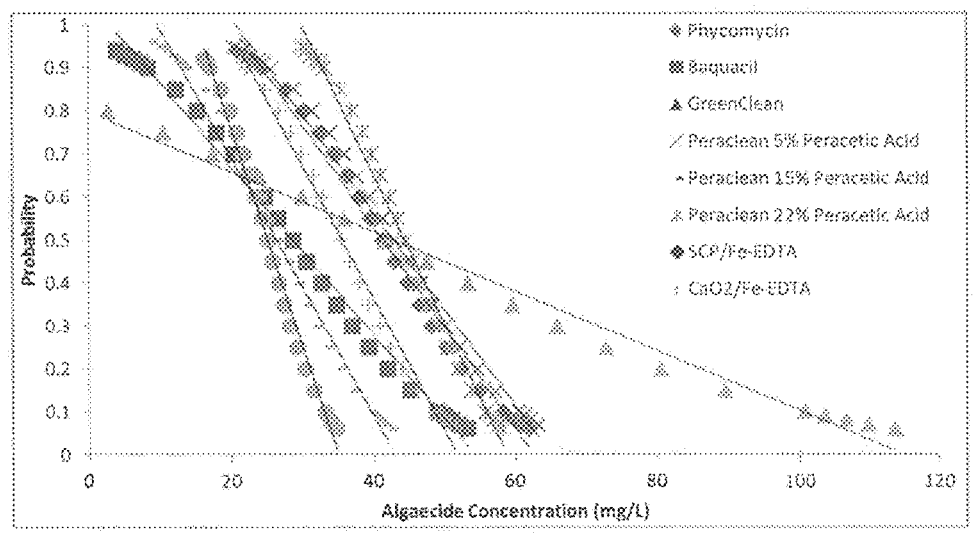
Probit plots for *P. subcapitata* responses in terms of cell density following exposures to a series of concentrations of peroxide-based algaecides.

_US 10,244,762 B1_

SOLID AQUATIC ORGANISM CONTROL COMPOSITION AND METHOD OF USE

RELATED APPLICATIONS

The present application is based on and claims priority to U.S. Provisional Patent application Ser. No. 62/299,656, filed on Feb. 25, 2016, which is incorporated herein by reference.

BACKGROUND

Many different pesticides, such as herbicides and algaecides, are commercially available for controlling unwanted plant and algae populations. The herbicides and algaecides are designed to limit growth and/or destroy a particular plant or algae or a broad range of plants and algae. The herbicide or algaecide may function in different ways. For instance, some herbicides and algaecides inhibit plant or algae growth by inhibiting photosynthesis. Other herbicides or algaecides are designed to be taken in by the plant or algae for inhibiting enzyme production. Other herbicides or algaecides may work as an oxidizer or may regulate plant growth by serving as an auxin mimic.

Of particular importance is that the herbicide or algaecide be capable of controlling growth or destroying a plant or algae population without harming the environment. For example, ideally a herbicide or algaecide will control plant or algae growth without having significant long-term adverse impacts on non-target organisms in the environment.

Particular problems are faced when attempting to control plant and algae growth in an aquatic environment, particularly in areas of high water exchange. Under these circumstances, the application of the herbicide or algaecide in controlled amounts can be difficult. Given the use sites for aquatic herbicides and algaecides, a margin of safety for non-target organisms must be met, and therefore very small amounts of herbicides or algaecides are permitted for use in many aquatic environments. These low concentrations, however, may not be sufficient to control particular plant or algae population, given environmental conditions as those described above.

Some pesticides and antimicrobial agents are known to contain hydrogen peroxide. Hydrogen peroxide has advantages and benefits when used in an aquatic environment because it decomposes to oxygen and water and therefore is relatively safe to use. Another advantage to hydrogen peroxide is that it has a broad spectrum of biocidal activities against many different types of organisms. Unfortunately, however, hydrogen peroxide can have a relatively low rate of activity.

One commercial algaecide that produces hydrogen peroxide in aquatic environments is Phycomycin SCP available from Lonza, Inc. Phycomycin SCP is a sodium carbonate peroxyhydrate based algaecide that has proven to be very effective in many applications. The algaecide, for instance, is an excellent tool for use in small ponds where oxygen depletion may be a concern. In addition to controlling algae, for instance, the algaecide also produces oxygen in the water column.

Although phycomycin SCP is a proven and effective algaecide, further improvements in the art are still needed. In particular, a need exists for a storage stable algaecide oxidizer that has enhanced effectiveness or potency.

SUMMARY

The present disclosure is generally directed to an antimicrobial composition that is effective against a broad range of microorganisms. The composition is particularly well suited for use in aquatic environments for controlling algae and/or bacteria, and cyanobacteria. The aquatic organism control composition of the present disclosure is extremely stable during storage, is easy to handle, can be distributed in controlled amounts, and is safe and non-hazardous when dispensed into the environment. The aquatic organism control composition is also well suited to reducing the populations of problematic organisms even when diluted to very low concentrations.

In general, the aquatic organism control composition of the present disclosure contains a hydrogen peroxide producing compound in combination with a plurality of additives that increase the oxidizing potential of the hydrogen peroxide producing compound. The aquatic organism control composition of the present disclosure is in the form of a solid such as a powder, a flake, a granule, a pellet, a tablet, a briquette, a unit dose or other solid form. When placed in an aqueous medium, the composition produces a relatively long lasting and potent amount of hydrogen peroxide that acts as a biocide to destroy microorganisms and/or to prevent the growth of microorganisms, such as bacteria and algae.

The hydrogen peroxide producing compound may comprise, for instance, a percarbonate, a urea-hydrogen peroxide complex, a perborate, or mixtures thereof. In one embodiment, for instance, the hydrogen peroxide producing compound may comprise sodium perborate. In another embodiment, the hydrogen peroxide producing compound may comprise sodium carbonate peroxyhydrate or potassium carbonate peroxyhydrate. The hydrogen peroxide producing compound can be present in the composition in an amount greater than or equal to about 75% by weight, such as in an amount greater than or equal to about 80% by weight, such as in an amount greater than or equal to about 85% by weight, such as in an amount greater than or equal to about 90% by weight, such as in an amount greater than or equal to about 95% by weight, such as in an amount greater than or equal to about 96% by weight, such as in an amount greater than or equal to about 97% by weight, such as in an amount greater than or equal to about 98% by weight. In one embodiment, for instance, the hydrogen peroxide producing compound is present in the composition in an amount from about 95% to about 99.5% by weight, such as in an amount from about 96% to about 99.5% by weight.

In accordance with the present disclosure, the hydrogen peroxide producing compound is combined with a chelating agent and a peroxide enhancing agent. The chelating agent may comprise, for instance, a solid aminocarboxylate. In one embodiment, the chelating agent comprises ethylenediaminetetraacetic acid (EDTA) and salts thereof, particularly metal salts thereof such as an iron salt. Other examples of chelating agents include nitrilotriacetic acid (NTA), N-hydroxyethyl,N,N,N''-ethylenediaminetriacetic acid (HEDTA), diethylenetriaminepentaacetic acid (DTPA), N,N,N',N transdiaminocyclohexanetetraacetic acid (CDTA), N-hydroxyethyliminodiacetic acid (HIMDA), gluconic acid, salicylic acid, 3,5 disulfopyrocatechol (Tiron), ethylenediamine-N,N'-disuccinic acid (EDDS); (2-hydroxyethyl)-imino-diacetic acid (HEIDA); L-glutamic acid-N,N-di-(acetic acid) (GLDA); ethylenediamine-N,N'-diacetic acid (EDDA); or hydroxyethylethylene-diaminotriacetic acid (HEDTA), or mixtures thereof.

In addition to a chelating agent, the hydrogen peroxide producing compound is also combined with a peroxide enhancing agent. The peroxide enhancing agent, for instance, may comprise phenol, 2-chlorophenol, 3-chlorophenol, 4-chlorophenol, 2,4 dichlorophenol, 2,4,6-trichlorophenol, caffeic acid, a hydroxyphenol, a hydroxylbenzoic acid, a cuprous ion compound, or mixtures thereof.

In one embodiment, the peroxide enhancing agent comprises an α-hydroxylcarboxylic acid. For instance, the α-hydroxylcarboxylic acid may comprise lactic acid, glycolic acid, malic acid, tartaric acid, 2-hydroxyisobutyric acid, citric acid or mixtures thereof. In one particular embodiment, the peroxide enhancing agent comprises citric acid.

In one embodiment, the peroxide enhancing agent is present in the composition in an amount greater than the chelating agent. For instance, the chelating agent and the peroxide enhancing agent may be present in the composition at a weight ratio of from about 1:1 to about 1:10, such as from about 1:1 to about 1:5. In one embodiment, the weight ratio can be from about 1:1.25 to about 1:3, such as from about 1:1.5 to 1:2.

In one embodiment, the aquatic organism control composition contains sodium carbonate peroxyhydrate in combination with Fe-EDTA and citric acid. The hydrogen peroxide producing compound can be present in an amount from about 90% to about 99.9% by weight. The chelating agent can be present in an amount from about 0.1% to about 2% by weight, while the peroxide enhancing agent may be present in an amount from about 0.5% to about 10% by weight.

In one embodiment, the chelating agent and the peroxide enhancing agent are combined with the hydrogen peroxide producing compound so as to control an algae population in an aqueous medium. The algae population, for instance, may comprise *Pseudokirchneriella subcapitata*. For instance, the chelating agent and peroxide enhancing agent can be present in the composition in an amount sufficient to increase the efficacy of the hydrogen peroxide producing composition against the above algae in comparison to use of the hydrogen peroxide producing compound alone. The increased efficacy, for instance, can be measured when the aqueous medium contains the algae at a cell density of $10^6$ cells/mL and the concentration of the composition can be 30 mg algaecide/L.

The present disclosure is also directed to a method of controlling the growth of a plant or algae population comprising contacting a plant, algae or cyanobacteria or bacteria with the aquatic organism control composition as described above. The plant, algae or cyanobacteria or bacteria can be contained in a body of water and contacted with the aquatic organism control composition by adding the aquatic organism control composition to the body of water. In one embodiment, the composition is added to the water sufficient for the composition to produce a hydrogen peroxide concentration of from about 1 ppm to about 30 ppm, such as from about 3 ppm to about 15 ppm. In one embodiment, the aquatic organism control composition may comprise a free-flowing granular composition that is added to the body of water.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying FIGURE, in which:

FIG. 1 is a graph illustrating *Pseudokirchineriella subcapitata* responses in terms of cell density following exposures to a series of concentrations of peroxide-based algaecides.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to an antimicrobial composition that contains an oxidizing agent for destroying and/or limiting the population of an organism. The present disclosure is more particularly directed to an aquatic organism control composition for controlling the population of organisms in an aquatic environment, such as algae, cyanobacteria, and/or bacteria.

The aquatic control composition of the present disclosure generally contains a hydrogen peroxide producing compound in combination with a mixture of adjuvants. In one embodiment, for instance, the hydrogen peroxide producing compound is combined with at least one chelating agent and at least one peroxide enhancing agent. The mixture of adjuvants has been found to dramatically increase the efficacy and the potency of the hydrogen peroxide producing source when dispersed in an aqueous medium. Hydrogen peroxide is a known effective biocide that can have a relatively slow kill rate. The combination of components according to the present disclosure produces a composition that is not only in an easy to handle solid form and is storage stable, but that also has enhanced biocide and particularly algaecidal properties.

For instance, the composition of the present disclosure, in certain embodiments, is at least 1.5, such as at least 1.75, such as at least 2, such as at least 2.25, such as at least 2.5, such as at least 2.7 times more active against a target organism than when the target organism is contacted with the hydrogen peroxide producing compound alone. In one embodiment, for instance, the algaecide potency of a commercially available algaecide, sodium carbonate peroxyhydrate, can be increased from about 1.5 to about 2.5 times against certain algae species, such as *Pseudokirchinerilla subcapitata*.

The composition of the present disclosure can be used in numerous and diverse applications. For instance, the composition has antimicrobial properties. The composition is particularly well suited for use as an aquatic organism control composition. For instance, the composition may be used for algae and/or bacteria control in small or large bodies of water. For instance, the composition can be used to control algae and/or bacteria in ponds, pools, public fountains, on marine vessels and marine equipment, and the like.

The aquatic organism control composition of the present disclosure is efficacious against a wide variety of microorganisms, including bacteria, cyanobacteria, and algae.

The composition of the present disclosure generally contains a hydrogen peroxide producing compound in combination with a chelating agent and a peroxide enhancing agent. The hydrogen peroxide producing compound may comprise a compound containing a peroxy moiety. The hydrogen peroxide producing compound may also comprise a hydrogen peroxide adduct containing molecular hydrogen peroxide. More particularly, the hydrogen peroxide producing compound comprises a compound that on dissolution in water liberates hydrogen peroxide into solution. In one embodiment, the hydrogen peroxide producing compound comprises a solid.

Examples of hydrogen peroxide producing compounds that may be used in accordance with the present disclosure include a percarbonate, such as a metal percarbonate, a urea-hydrogen peroxide complex, a perborate, such as a metal perborate, a peroxyhydrate, or mixtures thereof. Examples of hydrogen peroxide producing compounds that may be used include alkali metal percarbonates, such as sodium percarbonate, potassium percarbonate, rubidium percarbonate, cesium percarbonate, and mixtures thereof. The hydrogen peroxide producing compound may also comprise a urea peroxyhydrate, a peroxyacetyl borate, sodium perborate, ammonium carbonate peroxyhydrate, a hydrogen peroxide polyvinyl pyrrolidone, and mixtures thereof.

In one embodiment, the hydrogen peroxide producing compound comprises sodium carbonate peroxyhydrate. Sodium carbonate peroxyhydrate is a solid that can be produced in granular form. When dissolved in water, sodium carbonate peroxyhydrate releases hydrogen peroxide and sodium carbonate.

The hydrogen peroxide producing compound may be considered an oxidizing agent that releases hydrogen peroxide. The hydrogen peroxide oxidizes and thus kills the targeted organism. Hydrogen peroxide, for instance, reacts with smaller organisms, such as simple celled organisms, and kills on contact most forms of algae, cyanobacteria, bacteria, fungi, viruses, mosses, liverworts, hornworts, lichens, and the like. Of particular advantage, after contact, the hydrogen peroxide breaks down into water and oxygen.

The hydrogen peroxide producing compound is present in the composition of the present disclosure in relatively great amounts. For instance, the hydrogen peroxide producing compound can be present in the composition in an amount greater than or equal to about 75% by weight, such as in an amount greater than or equal to about 80% by weight, such as in an amount greater than or equal to about 85% by weight, such as in an amount greater than or equal to about 90% by weight, such as in an amount greater than or equal to about 93% by weight, such as in an amount greater than or equal to about 95% by weight, such as in an amount greater than or equal to about 96% by weight, such as in an amount greater than or equal to about 97% by weight, and may be present in amounts up to about 99.5% by weight. For instance, in one embodiment, the hydrogen peroxide producing compound is present in the composition in an amount from about 96% by weight to about 99.5% by weight.

In order to dramatically improve the efficacy of the hydrogen peroxide producing compound, the hydrogen peroxide producing compound in accordance with the present disclosure is combined with a chelating agent and a peroxide enhancing agent. Compositions made according to the present disclosure, for instance, can more than double the activity of the hydrogen peroxide producing compound when dispersed in an aqueous medium. Of particular advantage, the efficacy or potency of the hydrogen peroxide producing compound is increased by adding relatively small amounts of the adjuvants.

The peroxide enhancing agent may comprise, in one embodiment, an acid, such as a carboxylic acid or salt thereof, a hydroxy-containing compound, or a compound containing a cuprous ion. In one embodiment, for instance, the peroxide enhancing agent comprises an α-hydroxylcarboxylic acid. The α-hydroxylcarboxylic acid, for instance, may comprise citric acid, lactic acid, glycolic acid, 2-hydroxyisobutyric acid, malic acid, tartaric acid, or mixtures thereof. In certain embodiments, a salt, such as a sodium or potassium salt of one of the above acids may be used. In an alternative embodiment, the peroxide enhancing agent may comprise phenol, 2-chlorophenol, 3-chlorophenol, 4-chlorophenol, 2,4 dichlorophenol, 2,4,6-trichlorophenol, caffeic acid. In another embodiment, the peroxide enhancing agent may comprise a hydroxyphenol, such as catechol. In another embodiment, the peroxide enhancing agent may comprise a hydroxylbenzoic acid, such as para-hydroxylbenzoic acid, meta-hydroxybenzoic acid, gallic acid, or mixtures thereof. Any and all of the above peroxide enhancing agents may be blended together and combined with the hydrogen peroxide producing compound.

Although unknown, it is believed that the peroxide enhancing agent enhances hydroxy radical formation, especially when the composition is dispersed in an aqueous environment. In this regard, the peroxide enhancing agent improves efficacy. In addition, it is believed that the peroxide enhancing agent may complex with iron in solution.

The peroxide enhancing agent is present in the composition generally in an amount less than or equal to about 10% by weight, such as in an amount less than or equal to about 8% by weight, such as in an amount less than or equal to about 6% by weight. The peroxide enhancing agent is generally present in an amount greater than or equal to about 0.5% by weight, such as in an amount greater than or equal to about 1% by weight, such as in an amount greater than or equal to about 1.5% by weight. In one embodiment, the peroxide enhancing agent is present in the composition in an amount from about 0.5% by weight to about 5% by weight, such as in an amount from about 0.5% by weight to about 2% by weight. In general, the peroxide enhancing agent is present in the composition in amounts greater than the chelating agent.

In addition to the peroxide enhancing agent, the composition also contains a chelating agent. The chelating agent synergistically works in conjunction with the peroxide enhancing agent to dramatically increase the potency of the hydrogen peroxide producing compound. The chelating agent serves as a stabilizer for the hydrogen peroxide producing compound. The chelating agent may also stabilize hydrogen peroxide when dispersed in an aquatic environment. In addition, the present inventors discovered that the combination of a chelating agent and a peroxide enhancing agent dramatically improves the potency and effectiveness of the composition in limiting and destroying populations of microorganisms, such as algae, cyanobacteria, and bacteria. The synergistic effect between the chelating agent and the peroxide enhancing agent is unexpected.

In one embodiment, the chelating agent may comprise a solid aminocarboxylate. For instance, in one embodiment, the chelating agent may comprise a salt of ethylenediaminetetraacetic acid (EDTA). Examples of chelating agents that may be used include nitrilotriacetic acid (NTA), N-hydroxyethyl,N,N,N"-ethylenediaminetriacetic acid (HEDTA), diethylenetriaminepentaacetic acid (DTPA), N,N,N',N transdiaminocyclohexanetetraacetic acid (CDTA), N-hydroxyethyliminodiacetic acid (HIMDA), gluconic acid, salicylic acid, 3,5 disulfopyrocatechol (Tiron), ethylenediamine-N,N'-disuccinic acid (EDDS); (2-hydroxyethyl)-imino-diacetic acid (HEIDA); L-glutamic acid-N,N-di-(acetic acid) (GLDA); ethylenediamine-N,N'-diacetic acid (EDDA); or hydroxyethylethylene-diaminotriacetic acid (HEDTA), or mixtures thereof.

In one embodiment, an aminocarboxylate chelating agent is used that generates an iron complex. In one particular embodiment, Fe-EDTA is used as the chelating agent. Fe-EDTA may be used alone or in conjunction with any of the above chelating agents. In an alternative embodiment, a combination of any of the above chelating agents may be used. Copper salts may also be used as an alternative to iron salts.

In general, the chelating agent may be present in the composition in an amount from about 0.1% to about 2% by weight. For instance, the chelating agent may be present in the composition in an amount greater than or equal to about 0.2% by weight, such as in an amount greater than or equal to about 0.4% by weight, such as in an amount greater than or equal to about 0.5% by weight. The chelating agent is generally present in an amount less than or equal to about 1.5% by weight, such as in an amount less than or equal to about 1% by weight.

As described above, in one embodiment, the peroxide enhancing agent may be present in the composition in amounts greater than the chelating agent. For example, the weight ratio of the chelating agent to the peroxide enhancing agent can be from about 1:1.1 to about 1:10, such as from about 1:1.25 to about 1:5. In one embodiment, the weight ratio can be from about 1:1.25 to about 1:3, such as from about 1:1.5 to about 1:2.

Of particular advantage, the relative proportionate amounts of the chelating agent and the peroxide enhancing agent in a composition can be controlled in order to control the rate at which a hydrogen peroxide radical is produced when the composition is immersed in an aqueous medium. The greater amounts of chelating agent and peroxide enhancing agent that are present in the composition will generally increase radical formation.

The composition of the present disclosure can be produced solely with one or more hydrogen peroxide producing compounds, one or more chelating agents, and one or more peroxide enhancing agents. In fact, in one embodiment, the composition can be formulated so as to be free from phosphorus containing compounds, such as phosphates, phosphonates, phosphinic acids, and the like.

Optionally, the composition may contain various other ingredients. For instance, in one embodiment, small amounts of one or more surfactants may be present in the composition. Surfactants that are useful in the compositions described herein may be either non-ionic, anionic, amphoteric or cationic, or a combination of any of the above, depending on the application. Suitable non-ionic surfactants include alkanolamides, amine oxides, block polymers, ethoxylated primary and secondary alcohols, ethoxylated alkylphenols, ethoxylated fatty esters, sorbitan derivatives, glycerol esters, propoxylated and ethoxylated fatty acids, alcohols, and alkyl phenols, alkyl glucoside glycol esters, polymeric polysaccharides, sulfates and sulfonates of ethoxylated alkylphenols, and polymeric surfactants. Suitable anionic surfactants include ethoxylated amines and/or amides, sulfosuccinates and derivatives, sulfates of ethoxylated alcohols, sulfates of alcohols, sulfonates and sulfonic acid derivatives, and polymeric surfactants. Suitable amphoteric surfactants include betaine derivatives. Suitable cationic surfactants include amine surfactants. Those skilled in the art will recognize that other and further surfactants are potentially useful in the compositions depending on the particular application.

Other additives that may be present in the composition include corrosion inhibitors, emulsifiers, fragrances, dyes, preservatives, antifoam agents, and mixtures thereof.

The composition of the present disclosure is formulated to be a solid. In one embodiment, the solid can be in granular form. As used herein, granular form includes small particle sizes such as powders and refers to a composition being comprised of particles and is to be distinguished from dispersions, suspensions or gels. In one embodiment, the composition can be comprised of particles in a free-flowing state.

In addition to being in granular form, the composition may comprise a pellet, a tablet, a puck, or a solid block comprised of a single dose or multiple doses that can be easily separated.

The composition of the present disclosure can be used to treat all different types of small organisms, including bacteria, plants, cyanobacteria, and algae. The composition, for instance, may comprise an aquatic organism control composition for controlling aquatic algae populations and bacteria populations. Bodies of water that may be treated include fresh water systems such as lakes, streams, creeks, reservoirs, water canals, ponds, and the like.

When treating water bodies, the composition can be added to an aqueous system such that the concentration of hydrogen peroxide in the water is from about 0.001 ppm to about 50 ppm, such as from about 1 ppm to about 30 ppm, such as from about 3 ppm to about 15 ppm. In one embodiment, the composition is added such that the hydrogen peroxide concentration is less than or equal to about 40 ppm, such as less than or equal to about 30 ppm, such as less than or equal to about 20 ppm. The hydrogen peroxide concentration can be greater than or equal to about 2 ppm, such as greater than or equal to about 5 ppm. In one embodiment, the composition is added to a body of water such that the hydrogen peroxide concentration is from about 8 ppm to about 12 ppm, such as from about 9 ppm to about 10.5 ppm.

The present disclosure may be better understood with reference to the following example.

EXAMPLES

The following examples are provided to further illustrate the invention but not to limit its scope. Other variants of the invention will be readily apparent to one of ordinary skill in the art and are encompassed by the appended claims.

Example 1

A 96 hour static non-renewal algal toxicity test was conducted to measure the relative sensitivity of *Pseudokirchineriella subcaptata* to eight peroxide algaecides, identified in Table 1. *P. subcaptata* (UTEX 1648) was cultured in COMBO medium (Kilham et al. 1998) to a cell density of approximately $10^6$ cells/mL. A range finding experiment was designed to identify algaecide concentrations for the definitive algal toxicity test.

TABLE 1

| Description of peroxide-based algaecides | | |
| --- | --- | --- |
| Name | Parent Company | Description |
| Phycomycin-SCP | Lonza. inc. | 85.0% sodium carbonate peroxyhydrate |
| Baquacil Oxidizer | Lonza, Inc. | Chlorine-free; 27% specially-stabilized hydrogen peroxide |
| GreenClean | BioSafe Systems | 85% sodium carbonate peroxyhydrate |
| Peraclean 5% Peracetic Acid | Evonik industries | 5% peracetic acid; 26% hydrogen peroxide |
| Peraclean 15% Peracetic Acid | Eivonik industries | 15% peracetic acid; 21% hydrogen peroxide |
| Peraclean 22% Peracetic Acid | Evonik industries | 22% peracetic acid; |
| Phycomycin-SCP with Fe-EDTA and citric acid | Lonza, Inc. | Sodium carbonate peroxyhydrate; 0.6 % Fe-EDTA; 1% citric acid |
| Calcium peroxide with Fe-EDTA | Lonza, inc. | |

The experimental conditions for the definitive algal toxicity test are outlined in Table 2. To achieve nominal exposure concentrations, the appropriate masses of Phycomycin-SCP, Phycomycin-SCP with Fe-EDTA and citric acid, and calcium peroxide with Fe-EDTA were weighed and added to 1 L of algal suspension and mixed. The appropriate volumes of Baquacil Oxidizer and GreenClean were added to 1 L of algal suspension to achieve the nominal concentrations. Stock solutions at 10,000 mg algaecide/L of Peraclean 5 Peracetic Acid, Peraclean 15 Peracetic Acid and Peraclean 22 Peracetic acid were prepared, and the appropriate volumes of algaecide were added to 1 L to create nominal concentrations. Macroscopic images were taken and cell densities were measured 96 h after treatment. Cell densities were determined with a Neubauer Hemacytometer.

TABLE 2

Experimental design of toxicity experiments for *P. subcapitata* exposed to peroxide-based algaecides

| Algaecide | Initial Cell Density (cells/mL) | Number of Replicates | Nominal Algaecide Concentrations (mg algaecide/L) |
|---|---|---|---|
| Phycomycin-SCP | $2.41 \times 10^6$ | 3 | 0, 20, 30, 40, 50 and 60 |
| Baquacil Oxidizer | $2.01 \times 10^6$ | 3 | 0, 21, 29, 37, 45 and 53 |
| GreenClean | $2.41 \times 10^6$ | 3 | 0, 20, 62, 83, 123, 168 and 207 |
| Peraclean 5 Peracetic Acid | $2.41 \times 10^6$ | 3 | 0, 20, 30, 40, 50 and 60 |
| Peraclean 15 Peracetic Acid | $1.13 \times 10^6$ | 3 | 0, 10, 20, 30, 40, 50 and 60 |
| Peraciean 22 Peracetic acid | $2.41 \times 10^6$ | 3 | 0, 20, 30, 40, 50 and 60 |
| Phycomycin-SCP with Fe-EDTA and citric acid | $1.38 \times 10^6$ | 3 | 0, 10, 15, 20, 25, 30 and 35 |
| Calcium peroxide with Fe-EDTA | $1.38 \times 10^6$ | 3 | 0, 20, 25, 30, 35 and 40 |

Macroscopic images were taken of algal responses to a series of exposures for each algaecide. For each algaecide, the algal response was qualitatively determined based on color change from dark green to light green or clear. Exposure of *P. subcapitata* to the highest concentrations of Phycomycin-SCP (50 mg/L), Baquacil Oxidizer (53 mg/L), Peraclean 5 Peracetic Acid (60 mg/L), Peraclean 15 Peracetic Acid (60 mg/L), and calcium peroxide with Fe-EDTA (40 mg/L) revealed a color change from dark green to a lighter green. Exposure of *P. subcapitata* to the third highest concentration of GreenClean (123 mg/L) revealed a color change from dark green to a very pale green, while the two highest concentrations of GreenClean (168 mg/L and 207 mg/L) revealed a color change from dark green to clear. The highest concentrations of Peraclean 22 Peracetic Acid (60 mg/L) and Phycomycin-SCP with Fe-EDTA and citric acid (35 mg/L) also showed a significant color change from dark green to clear or a very pale green, respectively.

Exposure response relationships, which form a sigmoidal response curve, were quantitatively analyzed using the statistical procedure Probit. Probit plots of *P. subcapitata* responses to the eight different algaecides are displayed in FIG. 1. The Probit plots illustrate *P. subcapitata* responses in terms of cell density following exposures to a series of concentrations of peroxide-based algaecides. The solid black lines are predicted potency slopes. On the x-axis are the concentrations of different algaecides while on the y-axis are the predicted probabilities of live cells determined from the probit analysis.

Following an algaecide treatment, acceptable control of the algal species would be greater than 90% within 96 hours after treatment. $EC_{90}$ values, which are the effective concentrations where 90% of the organisms elicit a response (are made non-viable), were compared as shown in FIG. 1 and Table 3. Based on these $EC_{90}$ values, the differences in 96 h $EC_{90s}$ for Phycomycin-SCP, Baquacil Oxidizer, Peraclean 5 Peracetic Acid, Peraclean 15 Peracetic Acid, and Peraclean 22 Peracetic acid, and Calcium peroxide with Fe-EDTA are not statistically significant (Table 3). However, the 96 h $EC_{90s}$ for Phycomycin-SCP with Fe-EDTA and citric acid and for GreenClean are statistically different from the other algaecides tested (Table 3).

TABLE 3

96 h $EC_{90}$ values and potency slopes for *P. subcapitata* exposed to eight different peroxide algaecides in a static non-renewal laboratory toxicity tests.

| Algaecide | 96 h $EC_{90}$ (mg/L) and 95% fiducial limits | Potency Slope |
|---|---|---|
| Phycomycin-SCP | 58.21 (53.13-67.38) | −0.0235 |
| Baquacil Oxidizer | 48.97 (45.62-53.56) | −0.0195 |
| GreenClean | 100.88 (85.76-126.37) | −0.0069 |
| Peraclean 5 Peracetic Acid | 60.48 (56.74-65 95) | −0.0226 |
| Peraclean 15 Peracetic Acid | 39.41 (35.61-45.45) | −0.0299 |
| Peraclean 22 Peracetic acid | 55.81 (49.91-71.65) | −0.0345 |
| Phycomycin-SCP with Fe-EDTA and citric acid | 33.03 (31.44-35.18) | −0.0504 |
| Calcium peroxide with Fe-EDTA | 48.62 (44.02-57.91) | −0.0307 |

According to these $EC_{90}$ values, approximately 1.5 to 2 times more algaecide would have to be applied as Phycomycin-SCP, Baquacil Oxidizer, Peraclean 5 Peracetic Acid, Peraclean 15 Peracetic Acid, Peraclean 22 Peracetic acid, and Calcium peroxide with Fe-EDTA to achieve similar results as Phycomycin-SCP with Fe-EDTA and citric acid (FIG. 1 and Table 3). Approximately 3 times more algaecide would have to be applied as GreenClean to achieve similar results as Phycomycin-SCP with Fe-EDTA and citric acid (FIG. 1 and Table 3).

The potency slope is the effect of an incremental increase in exposure on the decrease in the response parameter (cell density). The potency slopes shown in FIG. 1 and Table 3 demonstrate that for each incremental increase in algaecide exposure for Phycomycin-SCP, Baquacil Oxidizer, Peraclean 5% Peracetic Acid, Peraclean 15% Peracetic Acid, Peraclean 22% Peracetic acid, Phycomycin-SCP with Fe-EDTA and citric acid and Calcium peroxide with Fe-EDTA, a greater algal response is elicited in comparison to Green-Clean.

The 96 h $EC_{90}$ for Peraclean 15% Peracetic Acid is likely an underestimate due to experimental error. Specifically, the samples were not constantly and uniformly exposed to a heat lamp. At the end of the 96 hour experiment the algal cells in the untreated control did not appear as healthy as did the untreated controls in the other experiments. This likely caused the *P. subcapitata* in this experiment to be more sensitive to the algaecide exposures.

Example 2

Tests were conducted similar to Example 1 to show the efficacy of compositions made according to the present disclosure against *Microcystis aeruginosa*. *M. aeruginosa* is a species of fresh water bacteria that can form harmful algal blooms.

The experimental conditions for the tests are outlined in Table 4 below.

TABLE 4

Exposures and experimental design of efficacy experiments for *M. aeruginosa*.

| Product | Targeted Concentration (mg $H_2O_2$/L) | Measured Concentration (mg $H_2O_2$/L) | Number of replicates/ concentration | Initial cell density (cells/mL) |
|---|---|---|---|---|
| Phycomycin-SCP | 2.8, 3.3, 4.1, 5.5, 6.1 | 2.1, 2.6, 3.3, 4.5, 4.9 | 3 | $3.1 \times 10^6$ |
| Phycomycin-SCP with Fe-EDTA and citric acid | 1.3, 2.1, 2.7, 3.2, 4.0 | 1.0, 1.5, 1.8, 2.3, 2.9 | 3 | $3.1 \times 10^6$ |

Peroxide concentrations were held constant at either 0.5 ppm, 1.5 ppm, 1.75 ppm, or 2.0 ppm. Fe-EDTA was applied at 0.3%, 0.6%, or 0.9% based on the original dry formulation. Citric acid was added at 1% based on the original dry formulation.

It was noticed during the test that when peroxide was applied at 1.75 ppm, the composition of the present disclosure significantly and dramatically performed better than the composition containing peroxide alone. For instance, Tables 5 and 6 below illustrate the differences when peroxide was applied at 1.75 ppm.

TABLE 5

In vivo chl a concentrations (µg/L ± SD) of *M. aeruginosa* cultures

| Time (days) | 1 0 ppm | 2 1.75 ppm $H_2O_2$ | 3 1.75 ppm $H_2O_2$ + 0.6% FeEDTA | 4 1.75 ppm $H_2O_2$ + 0.3% FeEDTA | 5 1.75 ppm $H_2O_2$ + 0.9% FeEDTA |
|---|---|---|---|---|---|
| 1 | 3.65 ± 0.04 | 2.87 ± 0.74 | 2.35 ± 0.07 | 2.39 ± 0.16 | 2.42 ± 0.05 |
| 2 | 3.77 ± 0.03 | 1.72 ± 0.66 | 1.27 ± 0.07 | 1.29 ± 0.08 | 1.31 ± 0.03 |
| 3 | 4.38 ± 0.17 | 1.31 ± 0.64 | 0.91 ± 0.02 | 0.94 ± 0.04 | 0.93 ± 0.01 |
| 4 | 5.32 ± 0.21 | 1.32 ± 0.63 | 0.95 ± 0.02 | 0.96 ± 0.02 | 0.96 ± 0.02 |

Initial in vivo chl a concentration = 3.83 ± 0.05 µg/L

TABLE 6

Cell density of *M. aeruginosa* cultures (cells/mL ± SD)

| Time (days) | 1 0 ppm | 2 1.75 ppm $H_2O_2$ | 3 1.75 ppm $H_2O_2$ + 0.6% FeEDTA | 4 1.75 ppm $H_2O_2$ + 0.3% FeEDTA | 5 1.75 ppm $H_2O_2$ + 0.9% FeEDTA |
|---|---|---|---|---|---|
| 4 | 4.0E+06 ± 1.0E+06 | 8.0E+04 ± 1.2E+05 | <1E+04 | <1E+04 | <1E+04 |

Initial cell density = 2.2E+06 ± 7.2E+04 cells/mL

Table 7 below shows peroxide concentrations necessary to achieve a decrease in cell density relative to the untreated control and a 90% decrease in cell density.

TABLE 7

$H_2O_2$ concentrations necessary to achieve a decrease in cell density relative to the untreated control and a 90% decrease in cell density.

| Product | Significant decrease in cell density compared to the untreated control | | 90% decrease in cell density |
|---|---|---|---|
| | mg $H_2O_2$/L | p-value | mg $H_2O_2$/L |
| Phycomycin-SCP | 2.1 | <0.0001 | 4.9 |
| Phycomycin-SCP with Fe-EDTA and citric acid | 2.3 | 0.0439 | 2.9 |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A solid aquatic organism control composition comprising:
   a hydrogen peroxide producing compound capable of releasing hydrogen peroxide when contacted with an aqueous medium;
   a chelating agent comprising an aminocarboxylate;
   a peroxide enhancing agent comprising a carboxylic acid or salt thereof, a hydroxyl-containing compound, a compound containing a cuprous ion, or combinations thereof; and wherein the hydrogen peroxide producing compound is present in the composition in an amount greater than or equal to about 85% by weight and the chelating agent is present in the composition in an amount of from about 0.1% to about 1.5% by weight.

2. The solid aquatic organism control composition as defined in claim 1, wherein the chelating agent and the peroxide enhancing agent are present in the composition in amounts and at ratios sufficient to enhance the efficacy of the composition against an algae species in comparison to the hydrogen peroxide producing compound alone.

3. The solid aquatic organism control composition as defined in claim 2, wherein the algae species comprises *Pseudokirchneriella subcapitata* and the comparison is when the algae species is present in water at a concentration of $10^6$ cells/mL and the concentration of the aquatic organism control composition is at a concentration of 30 mg/L.

4. The solid aquatic organism control composition as defined in claim 1, wherein the peroxide enhancing agent is present in the composition in amounts greater than the chelating agent.

5. The solid aquatic organism control composition as defined in claim 1, wherein the chelating agent and the peroxide enhancing agent are present in the composition at a weight ratio of from 1:1 to 1:10.

6. The solid aquatic organism control composition as defined in claim 1, wherein the hydrogen peroxide producing compound comprises a metal percarbonate, a urea-hydrogen peroxide complex, a perborate, or mixtures thereof.

7. The solid aquatic organism control composition as defined in claim 1, wherein the hydrogen peroxide producing compound comprises sodium carbonate peroxyhydrate.

8. The solid aquatic organism control composition as defined in claim 1, wherein the chelating agent comprises a solid aminocarboxylate.

9. The solid aquatic organism control composition as defined in claim 1, wherein the chelating agent comprises nitrilotriacetic acid (NTA), N-hydroxyethyl,N,N,N''-ethylenediaminetriacetic acid (HEDTA), diethylenetriaminepentaacetic acid (DTPA), N,N,N',N transdiaminocyclohexanetetraacetic acid (CDTA), N-hydroxyethyliminodiacetic acid (HIMDA), ethylenediamine-N,N'-disuccinic acid (EDDS); (2-hydroxyethyl)-imino-diacetic acid (HEIDA); L-glutamic acid-N,N-di-(acetic acid) (GLDA); ethylenediamine-N,N'-diacetic acid (EDDA); hydroxyethylethylene-diaminotriacetic acid (HEDTA), ethylenediaminetetraacetic acid (EDTA), salts thereof, or mixtures thereof.

10. The solid aquatic organism control composition as defined in claim 1, wherein the chelating agent comprises Fe-EDTA.

11. The solid aquatic organism control composition as defined in claim 1, wherein the peroxide enhancing agent comprises phenol, 2-chlorophenol, 3-chlorophenol, 4-chlorophenol, 2,4 dichlorophenol, 2,4,6-trichlorophenol, caffeic acid, a hydroxyphenol, a hydroxybenzoic acid, a cuprous ion compound, or mixtures thereof.

12. The solid aquatic organism control composition as defined in claim 1, wherein the peroxide enhancing agent comprises an α-hydroxylcarboxylic acid and wherein the α-hydroxylcarboxylic acid comprises lactic acid, glycolic acid, 2-hydroxyisobutyric acid, citric acid, or mixtures thereof.

13. The solid aquatic organism control composition as defined in claim 1, wherein the peroxide enhancing agent comprises citric acid.

14. The solid aquatic organism control composition as defined in claim 1, wherein the hydrogen peroxide producing compound comprises sodium carbonate peroxyhydrate, the chelating agent comprises Fe-EDTA, and the peroxide enhancing agent comprises citric acid.

15. The solid aquatic organism control composition as defined in claim 14, wherein the hydrogen peroxide producing compound is present in the composition in an amount from about 85% to about 99.4% by weight, the chelating agent is present in the composition in an amount from about 0.1% to about 1.5% by weight, and citric acid is present in an amount from about 0.5% to about 10% by weight, the citric acid being present in amounts greater than the chelating agent.

16. A method of controlling growth of an aquatic organism comprising contacting the aquatic organism with the aquatic organism control composition as defined in claim 1.

17. A method as defined in claim 16, wherein the aquatic organism comprises an algae population.

18. A method as defined in claim 16, wherein the aquatic organism is contained in a body of water and the aquatic organism is contacted with the aquatic organism control composition by adding the composition to the body of water.

19. A method as defined in claim 16, wherein the aquatic organism comprises a bacteria, a plant, or a cyanobacteria.

20. A method of controlling growth of an aquatic organism comprising contacting the aquatic organism with a solid aquatic organism control composition, the solid aquatic organism control composition comprising:
a hydrogen peroxide producing compound capable of releasing hydrogen peroxide when contacted with an aqueous medium;
a chelating agent comprising an aminocarboxylate; and
a peroxide enhancing agent comprising a carboxylic acid or salt thereof, a hydroxyl-containing compound, a compound containing a cuprous ion, or combinations thereof;
wherein the hydrogen peroxide producing compound is present in the composition in an amount greater than or equal to about 85% by weight and the chelating agent is present in the composition in an amount of from about 0.1% to about 1.5% by weight,
wherein the aquatic organism is contained in a body of water and the aquatic organism is contacted with the aquatic organism control composition by adding the composition to the body of water, and
wherein the aquatic organism control composition is added to the body of water such that the composition produces a concentration of hydrogen peroxide of from about 1 ppm to about 30 ppm in the body of water.

* * * * *